(12) United States Patent
Tunac

(10) Patent No.: US 8,273,881 B2
(45) Date of Patent: Sep. 25, 2012

(54) PHENAZINE COMPOUNDS AND USE THEREOF IN AUTOIMMUNE AND INFLAMMATORY DISEASES

(75) Inventor: Josefino B. Tunac, Oxford, MI (US)

(73) Assignee: JJ Pharma, Inc., San Francisco, CA (US)

( * ) Notice: Subject to any disclaimer, the term of this patent is extended or adjusted under 35 U.S.C. 154(b) by 139 days.

(21) Appl. No.: 12/523,304

(22) PCT Filed: Jan. 16, 2008

(86) PCT No.: PCT/US2008/051226
§ 371 (c)(1), (2), (4) Date: Mar. 2, 2010

(87) PCT Pub. No.: WO2008/089283
PCT Pub. Date: Jul. 24, 2008

(65) Prior Publication Data
US 2010/0190799 A1    Jul. 29, 2010

Related U.S. Application Data

(60) Provisional application No. 60/885,164, filed on Jan. 16, 2007.

(51) Int. Cl.
*C07D 241/46* (2006.01)
(52) U.S. Cl. ........................................ 544/347
(58) Field of Classification Search .................. 544/347
See application file for complete search history.

(56) References Cited

U.S. PATENT DOCUMENTS

| | | |
|---|---|---|
| 3,681,331 A | 8/1972 | Leimgruber et al. |
| 3,758,681 A | 9/1973 | Hamill et al. |
| 3,929,790 A | 12/1975 | Leimgruber et al. |
| 4,024,142 A | 5/1977 | Campbell |
| 4,064,127 A | 12/1977 | Campbell |
| 5,637,591 A | 6/1997 | Ono et al. |
| 6,291,455 B1 | 9/2001 | Thomas et al. |
| 2002/0128381 A1 | 9/2002 | Jakobsen et al. |
| 2004/0175407 A1 | 9/2004 | McDaniel |

FOREIGN PATENT DOCUMENTS

GB    1 272 057    4/1972

OTHER PUBLICATIONS

PCT International Search Report and Written Opinion, PCT/US2008/051226, May 20, 2008, 8 Pages.
West, A., "Solid State Chemistry and its Applications," 1988, pp. 358 and 365, Wiley, New York.
European Patent Office, Supplementary European Search Report and Opinion, European Patent Application No. 08727783.6, May 12, 2011, five pages.
European Patent Office, Communication pursuant to Article 94(3) EPC, European Patent Application No. 08 727 783.6, May 16, 2012, 2 pages.
European Patent Office, Invitation pursuant to Article 94(3) and Rule 71(1) EPC, European Patent Application No. 08 727 783.6, Jun. 14, 2012, 3 pages.

*Primary Examiner* — Douglas M Willis
(74) *Attorney, Agent, or Firm* — Fenwick & West LLP

(57) ABSTRACT

The invention discloses compounds, compositions and methods useful for preventing and/or treating autoimmune diseases and inflammatory diseases. The methods and compositions utilize water-soluble phenazine compounds, or salts, or solvates thereof. These molecules can be delivered alone or in combination with agents which treat or prevent autoimmune diseases and inflammatory diseases such as those caused by arthritis and rheumatoid arthritis.

9 Claims, 5 Drawing Sheets

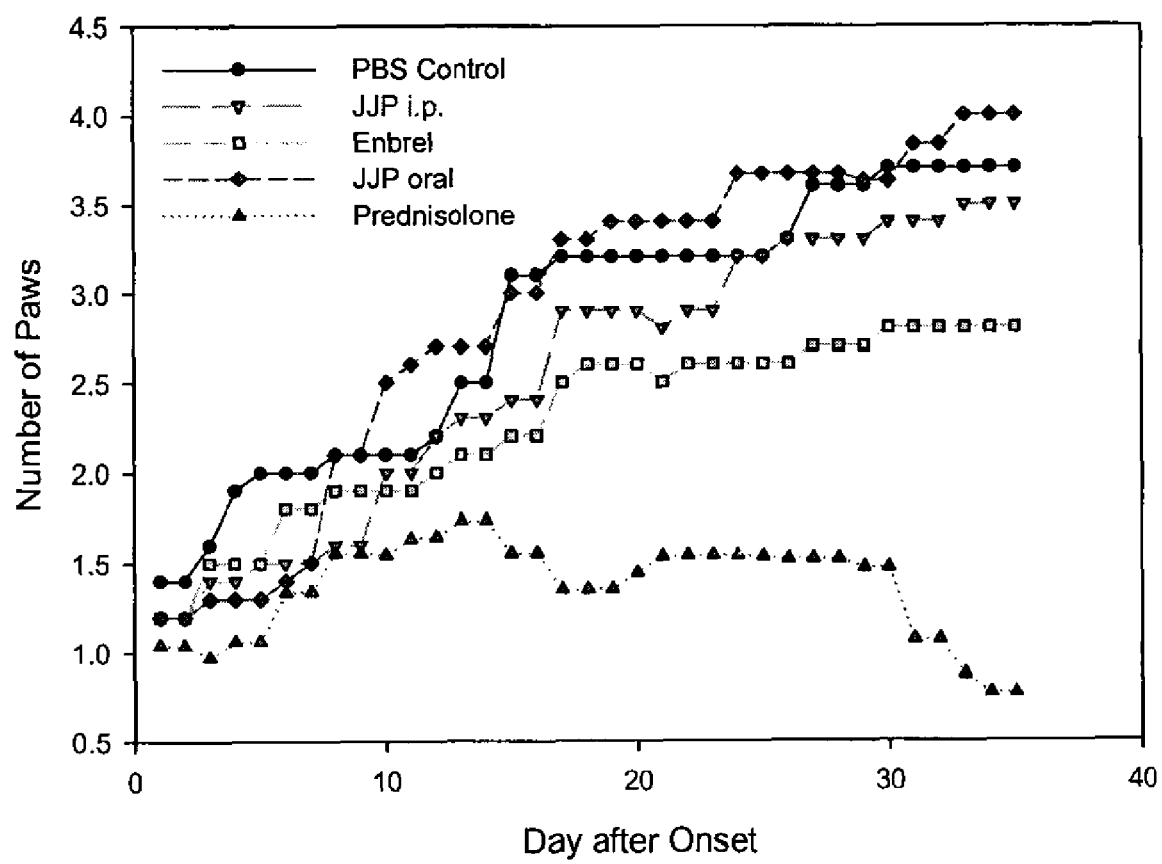
Figure 1 - Number of Arthritic Paws

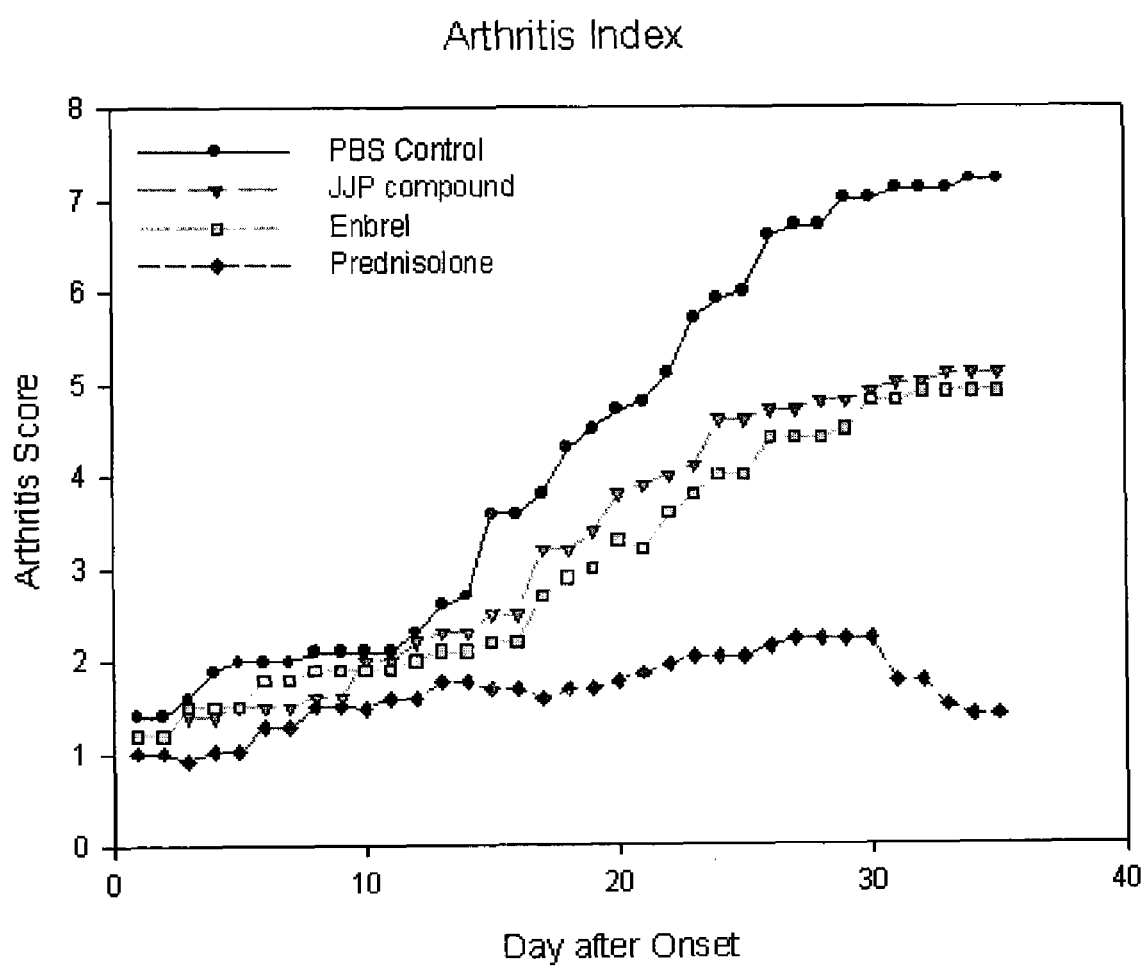
Figure 2. Overall arthritis score

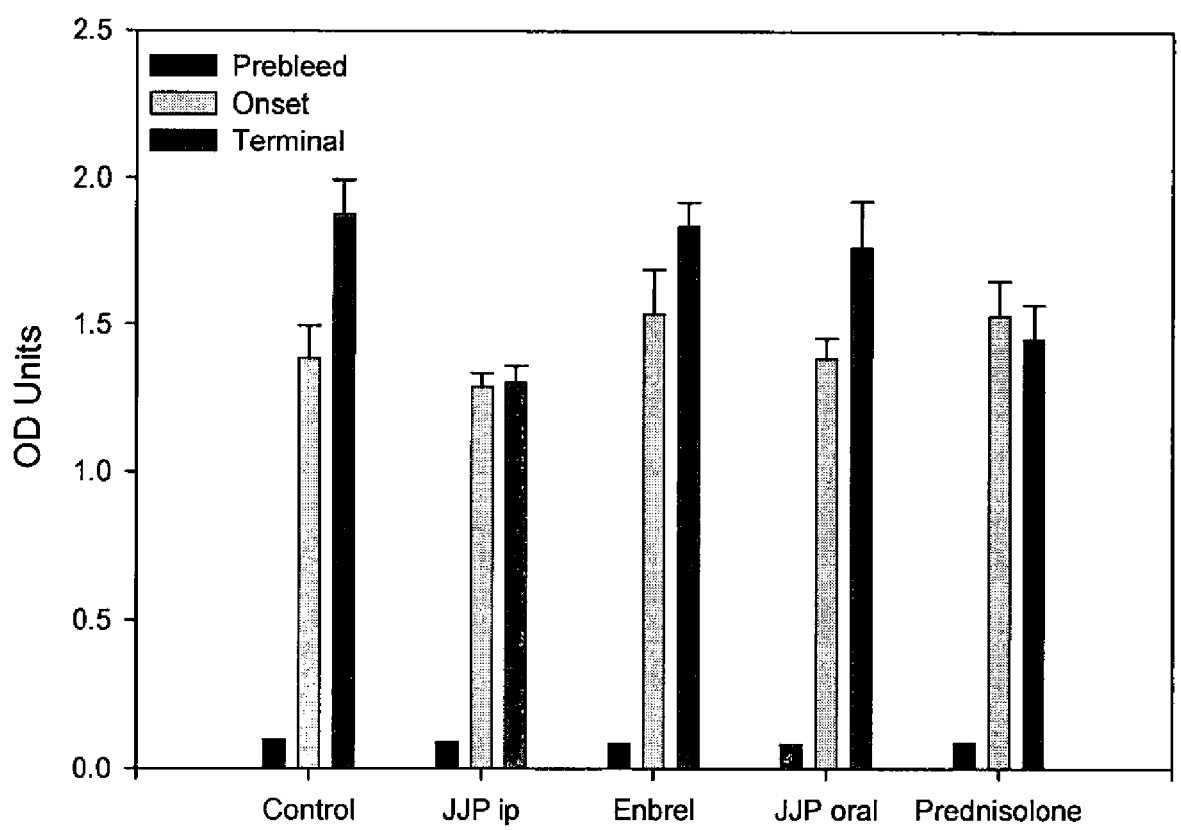

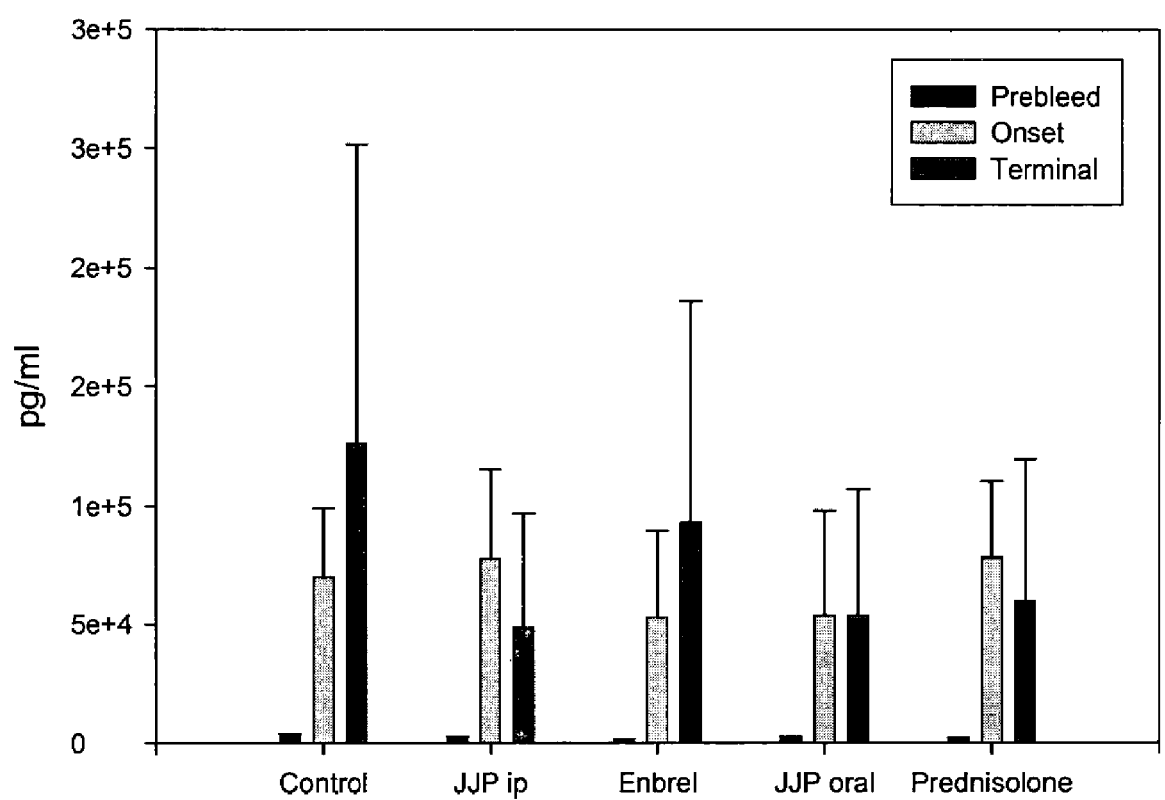
Figure 4 - Total Serum Immunoglobulin Levels

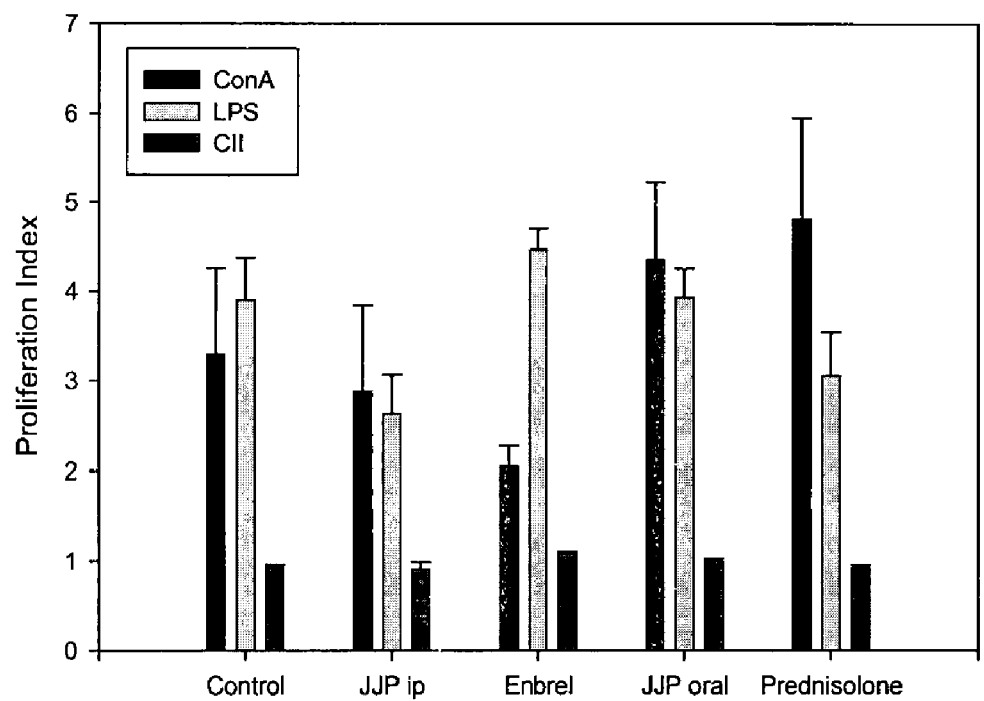
Figure 5 - Lymph Node Cell Responses
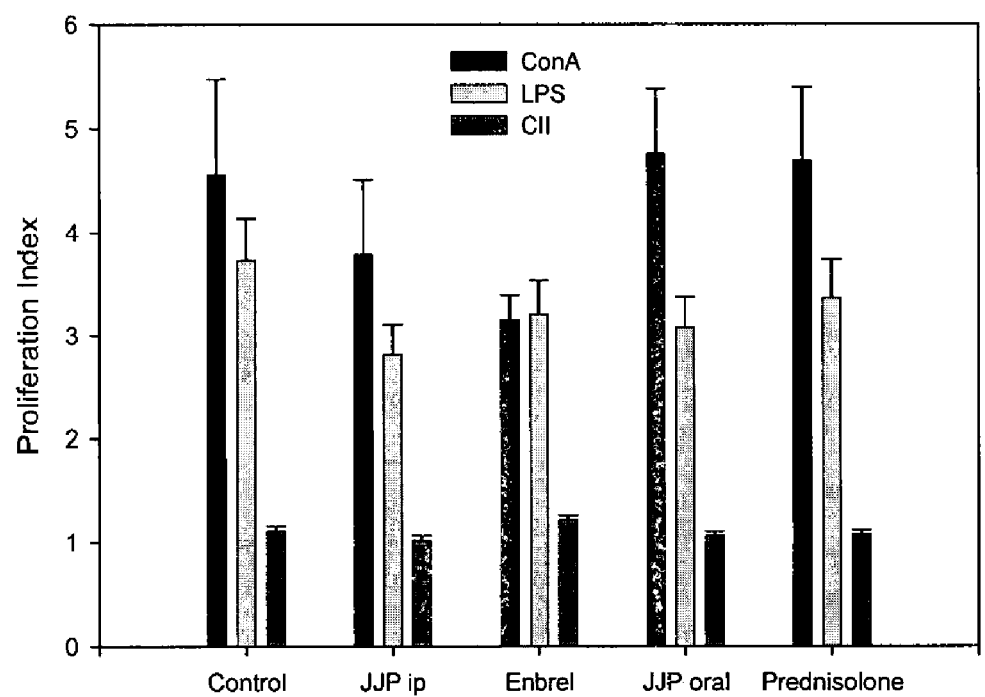
Figure 6 - Spleen Cell Responses

PHENAZINE COMPOUNDS AND USE THEREOF IN AUTOIMMUNE AND INFLAMMATORY DISEASES

CROSS-REFERENCE TO RELATED APPLICATIONS

This application is the National Stage of and claims priority to International Application No. PCT/US2008/051226, filed Jan. 16, 2008, and claims benefit of U.S. provisional Application No. 60/885,164, filed on Jan. 16, 2007, both of which are incorporated by reference in their entirety.

FIELD OF THE INVENTION

The present invention relates to novel water-soluble phenazine compounds, and their use in the treatment of autoimmune diseases and inflammatory diseases.

BACKGROUND OF THE INVENTION

Arthritis (from the Greek word for joint) is a chronic multifactorial disease induced when the immune system attacks and begins degrading the body's joints. Rheumatoid arthritis (RA) is characterized by chronic inflammation of the synovium, and comes in many forms, including calcific periarthritis, enteropathic arthritis, chronic, gouty, and hand osteoarthritis, hip and knee osteoarthritis, thumb, Jaccoud's, juvenile osteoarthritis, oligoarthritis, polyarthritis, and peripheral, psoriatic, rheumatoid, and septic arthritis. RA is triggered by an immune response generated via the molecular recognition of the T-cell receptor on CD4-positive T cells with a complex of disease-inducing peptides bound to Human Leukocyte Antigen (HLA) class II molecules.

Rheumatoid arthritis alone is estimated to affect 1% of the world's population and is twice as prevalent in women as in men. The aging population of developed countries are presents a growing market for arthritis therapies. In the US, arthritis and other rheumatic conditions affects about 15% of the population.

Rheumatoid arthritis is associated with the expression of certain HLA class II molecules. It is known that blockade of the interaction between a given class II molecule, peptide ligand, and T cell receptor inhibits specific T cell responses both in vitro and in vivo. Tumor necrosis factor α (TNFα), an inflammation-promoting cytokine is found associated with multiple inflammatory events, including arthritis, and anti-TNFα therapeutics include Enbrel® (Etanercept), Humira® (Adalimumab), and Remicade® (Infliximab).

Other therapeutic strategies which are directed at the T cell, such as total lymphoid irradiation, thoracic duct drainage, cyclosporin A, anti-CD4 monoclonal antibody, and other monoclonal antibodies directed at T cell determinants, result in some cases in clinical improvement of rheumatoid arthritis, but these therapies are also associated with side effects. For instance, conventional general immunosuppressives increase the risk of opportunistic infections and cancer.

There is no cure for arthritis or RA at present. Current therapies are aimed at alleviating the symptoms of the disease and arresting its progress using drugs such as Enbrel®. Chemotherapeutic agents such as methotrexate, cyclophosphamide and cyclosporine have been also used for alleviating symptoms. All of the above treatments have side-effect liabilities, limited effects on relapse rates and on ability to prevent exacerbation of the disease.

Thus, there is a need for new drugs which can be used alone or in combination with other drugs to combat the progression and symptoms of arthritis, in particular, RA. It has now been found that certain novel phenazine compounds facilitate recovery in subjects suffering from autoimmune diseases. Thus, the novel phenazine compounds are useful in the treatment and prevention of arthritis, RA, and other autoimmune diseases.

SUMMARY OF THE INVENTION

The present invention provides compositions and methods for treating or preventing the onset of autoimmune diseases, inflammation, inflammation diseases, metabolic syndrome, dyslipidemia, cardiovascular diseases, disorders of the peripheral and central nervous system, hematological diseases, cancer, respiratory diseases, gastroenterological diseases, diabetes, and non-alcoholic fatty liver disease. The molecules and compositions of the invention can be delivered alone or in combination with additional agents, and are used as for the treatment or prevention of autoimmune diseases, inflammation diseases, and cardiovascular diseases.

Accordingly, in one aspect, the subject invention is directed to a method for treating or preventing autoimmune diseases in a subject in need thereof. The method comprises administering to the subject a pharmaceutically effective amount of a compound of Formula I, II, III, or IV:

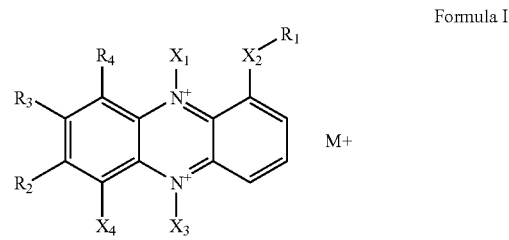

Formula I where $X_1$ and $X_3$ are independently selected to be $O^-$ or $S^-$; $X_2$ and $X_4$ are independently selected to be O, S, NH, $NR_5$ or $CHR_5$ where $R_5$ can be a lower alkyl; $R_1$ is selected from the group consisting of lower alkyl containing 1 to 10 carbon atoms, halo-lower alkyl, lower alkenyl, lower alkynyl, lower alkylasulfinyl, lower alkylsulfonyl, lower alkylthio, lower alkylamino, arylalkyl, substituted arylalkyl, cycloalkyl, substituted cycloalkyl, cycloheteroalkyl, substituted cycloheteroalkyl, heteroaryl, or substituted heteroaryl; $R_2$, $R_3$ and $R_4$ are independently selected to be hydrogen, lower alkyl, substituted lower alkyl, aryl, substituted aryl, arylalkyl, substituted arylalkyl, cycloalkyl, cyano, ether, halo, hydroxy, phosphate, phosphonate, sulfate, sulfonate, or sulfonamide; and $M^+$ can be alkali metal ion such as sodium, lithium, and potassium, alkaline earth metal ion such as calcium and magnesium, or any other positively charged species that forms a pharmaceutically acceptable salt.

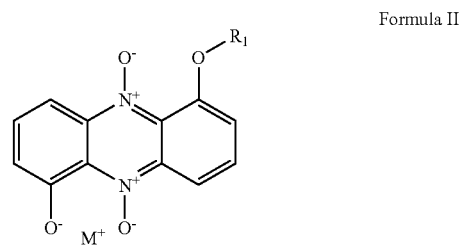

Formula II where $R_1$ can be lower alkyl containing 1 to 10 carbon atoms, halo-lower alkyl, lower alkenyl, lower alkynyl, lower alkylamino, cycloalkyl, or heteroaryl; and $M^+$ is $Na^+$, $K^+$, or any other positively charged species that forms a pharmaceutically acceptable salt.

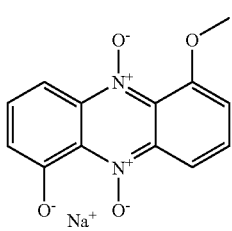

Formula III

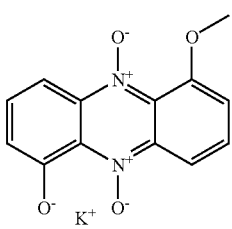

Formula IV

The invention thus provides methods for treating autoimmune disease in a mammalian subject in need thereof, the method comprising administering a pharmaceutically effective amount of a compound of Formula I, II, III, or IV.

In another aspect, the invention provides compounds comprising Formula II:

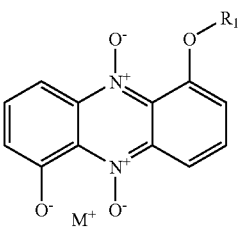

Formula II wherein $R_1$ is lower alkyl containing 1 to 10 carbon atoms, halo-lower alkyl, lower alkenyl, lower alkynyl, lower alkylamino, cycloalkyl, or heteroaryl, and $M^+$ is $Na^+$, $K^+$.

In yet another aspect, the present invention provides a pharmaceutical composition, which comprises a compound of Formula II and a pharmaceutically acceptable excipient. The excipient can be suitable for oral administration. Thus, the composition may be in the form of a tablet, a capsule, or a soft-gel capsule.

Alternatively, the excipient can be liquid suited to intravenous, intramuscular, or subcutaneous administration. Alternatively, the excipient may be suited to transdermal administration, or buccal administration.

In another aspect of the invention, a method of preparing a compound of Formula II is provided:

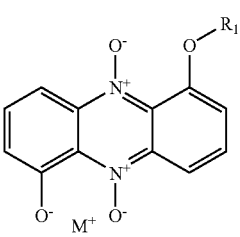

Formula II wherein $R_1$ is lower alkyl containing 1 to 10 carbon atoms, halo-lower alkyl, lower alkenyl, lower alkynyl, lower alkylamino, cycloalkyl, or heteroaryl; and $M^+$ is $Na^+$ or $K^+$ the method comprising growing *Lysobacter antibioticus* in agar culture medium (ACM) under favorable pH and temperature; inoculating a production culture medium (CPM) with the *Lysobacter antibioticus* and culturing under favorable pH and temperature with continuous agitation and aeration; extracting the compound from the CPM by using organic solvents; evaporating the organic solvent to provide crude intermediate; adding aqueous NaOH to an organic solution of crude intermediate; and recovering the compound by centrifugation.

These and other aspects of the present invention will become evident upon reference to the following detailed description. In addition, various references are set forth herein which describe in more detail certain procedures or compositions, and are therefore incorporated by reference in their entirety.

BRIEF DESCRIPTION OF FIGURES

FIG. 1 illustrates the progression of disease in the collagen-induced arthritis (CIA) mice based on the number of involved paws.

FIG. 2 illustrates the overall arthritis score assigned to the mice in the CIA model.

FIG. 3 illustrates the anti-type II collagen antibody levels in CIA mice.

FIG. 4 illustrates the total serum immunoglobulin levels in CIA mice.

FIG. 5 illustrates the lymph node cell responses to the mitogens concanavalin A and LPS, and the antigen response to type II collagen in CIA mice.

FIG. 6 illustrates the response of the spleen cells to the mitogens concanavalin A and LPS, and the antigen response to type II collagen in CIA mice.

DETAILED DESCRIPTION

I. Definitions

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (1992) "Advanced Organic Chemistry $3^{rd}$ Ed." Vols. A and B, Plenum Press, New York. The practice of the present invention will employ, unless otherwise indicated, conventional methods of mass spectroscopy, protein chemistry, biochemistry, recombinant DNA techniques and pharmacology, within the skill of the art.

The term "agonist" means a molecule such as a compound, a drug, an enzyme activator or a hormone that enhances the activity of another molecule or the activity of the a receptor site.

The term "antagonist" means a molecule such as a compound, a drug, an enzyme inhibitor, or a hormone, that diminishes or prevents the action of another molecule or the activity of the a receptor site.

"Alkyl" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl(allyl), cycloprop-1-en-1-yl, cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" specifically intended to include radicals having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl," are used. Preferably, an alkyl group comprises from 1-20 carbon atoms, more preferably, from 1 to 10 carbon atoms.

"Alkanyl" refers to a saturated branched, straight-chain or cyclic alkyl radical derived by the removal of one hydrogen atom from a single carbon atom of a parent alkane. Typical alkanyl groups include but are not limited to, methanyl; ethanyl; propanyls such as propan-1-yl, propan-2-yl(isopropyl), cyclopropan-1-yl, etc.; butanyls such as butan-1-yl, butan-2-yl(sec-butyl), 2-methyl-propan-1-yl(isobutyl), 2-methyl-propan-2-yl(t-butyl), cyclobutan-1-yl, etc.; and the like.

"Alkenyl" refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl, cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn3-yl, but-3-yn-1-yl, etc.; and the like.

"Acyl" refers to a radical —C(O)R, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to formyl, acetyl, cyclohexylcarbonyl, cyclohexylmethylcarbonyl, benzoyl, benzylcarbonyl and the like.

"Alkylamino" means a radical —NHR where R represents an alkyl, or cycloalkyl group as defined herein that may be optionally substituted by one or more substituents as defined herein. Representative examples include, but are not limited to, methylamino, ethylamino, 1-methylethylamino, cyclohexylamino and the like.

"Alkoxy" refers to a radical —OR where R represents an alkyl, or cycloalkyl group as defined herein that may be optionally substituted by one or more substituents as defined herein. Representative examples include, but are not limited to methoxy, ethoxy, propoxy, butoxy, cyclohexyloxy and the like.

"Alkylsulfonyl" refers to a radical —S(O)$_2$R where R is an alkyl, or cycloalkyl group as defined herein that may be optionally substituted by one or more substituents as defined herein. Representative examples include, but are not limited to, methylsulfonyl, ethylsulfonyl, propylsulfonyl, butylsulfonyl, and the like.

"Alkylsulfinyl" refers to a radical —S(O)R where R is an alkyl, or cycloalkyl group as defined herein that may be optionally substituted by one or more substituents as defined herein. Representative examples include, but are not limited to, methylsulfinyl, ethylsulfinyl, propylsulfinyl, butylsulfinyl, and the like.

"Alkylthio" refers to a radical —SR where R is an alkyl or cycloalkyl group as defined herein that may be optionally substituted by one or more substituents as defined herein. Representative examples include, but are not limited to methylthio, ethylthio, propylthio, butylthio, and the like.

"Amide or Acylamino" refers to a radical —NR'C(O)R", where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to, formylamino acetylamino, cyclohexylcarbonylamino, cyclohexylmethylcarbonylamino, benzoylamino, benzylcarbonylamino and the like.

"Amino" refers to the radical —NH$_2$.

"Aryl" refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorine, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleidene, pyrene, pyranthrene, rubicene, triphenylene, trinaphthalene, and the like. Preferable, an aryl group comprises from 6 to 20 carbon atoms, more preferably, between 6 to 12 carbon atoms.

"Carboxy" means the radical —C(O)OH.

"Cyano" means the radical —CN.

"Cycloalkyl" refers to a substituted or unsubstituted cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In a preferred embodiment, the cycloalkyl group is $(C_3-C_{10})$ cycloalkyl, more preferably $(C_3-C_7)$ cycloalkyl.

"Cycloheteroalkyl" refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like.

"Drug" refers to a compound that exhibits therapeutic and/or prophylactic and/or diagnostic utility when administered in effective amounts to a patient or a mammal.

"Ester" refers to a radical —C(O)OR, where R is alkyl, substituted alkyl, cycloalkyl, substituted cycloalkyl, cycloheteroalkyl, substituted cycloheteroalkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl as defined herein that may be optionally substituted by one or more substituents as defined herein. Representative examples include, but are not limited to, methyl ester (—C(O)OCH$_3$), cyclohexyl ester (—C(O)OC$_6$H$_{11}$), phenyl ester (—C(O)OC$_6$H$_5$), benzyl ester (—C(O)OCH$_2$C$_6$H$_5$), and the like.

"Ether" refers to a radical —OR, where R is alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Halo" means fluoro, chloro, bromo, or iodo.

"Heteroaryl" refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-20 membered heteroaryl, with 5-10 membered heteroaryl being particularly preferred. Preferred heteroaryl groups are those derived from thiophene, pyrrole, benzothiophene, benzofuran, indole, pyridine, quinoline, imidazole, oxazole and pyrazine.

"Hydroxy" means the radical —OH.

"Oxo" means the divalent radical =O.

As used herein, the term "patient" or "subject" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

"Pharmaceutically acceptable" means approved or approvable by a regulatory agency of the Federal or state government or listed in the U.S. Pharmacopoeia or other generally recognized pharmacopoeia for use in animals, and more particularly in humans. It can be material which is not biologically or otherwise undesirable, i.e., the material may be administered to an individual without causing any undesirable biological effects or interacting in a deleterious manner with any of the components of the composition in which it is contained.

The term "pharmaceutically acceptable salt" of a compound means a salt that is pharmaceutically acceptable and that possesses the desired pharmacological activity of the parent compound. Such salts, for example, include:
(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like;
(2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

"Pharmaceutically acceptable vehicle" refers to a diluent, adjuvant, excipient or carrier with which a compound of the invention is administered. The terms "effective amount" or "pharmaceutically effective amount" refer to a nontoxic but sufficient amount of the agent to provide the desired biological result. That result can be reduction and/or alleviation of the signs, symptoms, or causes of a disease, or any other desired alteration of a biological system. For example, an "effective amount" for therapeutic uses is the amount of the composition comprising one or more phenazine compounds disclosed herein required to provide a clinically significant decrease in autoimmune disease, such as those resulting from arthritis or rheumatoid arthritis, or from an inflammatory disease. An appropriate "effective" amount in any individual case may be determined by one of ordinary skill in the art using routine experimentation.

By "physiological pH" or a "pH in the physiologically acceptable range" is meant a pH in the range of approximately 7.2 to 8.0 inclusive, more typically in the range of approximately 7.2 to 7.6 inclusive.

"Preventing" or "Prevention" refers to a reduction in risk of acquiring a disease or disorder (i.e., causing at least one of the clinical symptoms of the disease not to develop in a patient that may be exposed to or preposed to the disease but does not yet experience or display symptoms of the disease).

"Prodrug" refers to a derivative of a drug molecule that requires a transformation within the body to release the active drug. Prodrugs are frequently (though not necessarily) pharmacologically inactive until converted to the parent drug.

"Protecting group" refers to a group of atoms that when attached to a reactive group in a molecule masks, reduces or prevents that reactivity. Examples of protecting groups can be found in Green et al., "Protective Groups in Organic Chemistry", (Wiley, 2$^{nd}$ ed. 1991) and Harrison et al., "Compendium of Synthetic Organic Methods", vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilylethanesulfonyl ("SES"), trityl and substituted trityl groups, allyloxycarbonyl, 9-fluorenylmethyloxycarbonyl ("FMOC"), nitroveratryloxycarbonyl ("NVOC") and the like. Representative hydroxyl protecting groups include, but are not limited to, those where the hydroxyl group is either acylated or alkylated such as benzyl, and trialkylsilyl ethers and allyl ethers.

"Substituted" refers to a group in which one or more hydrogen atoms are each independently replaced with the same or different substituents(s). Typical substituents include, but are not limited to, —X, —R$^{54}$, —O$^-$, =O, —OR$^{54}$, —SR$^{54}$, —S, =S, —NR$^{54}$R$^{55}$, =NR$^{54}$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$OR$^{54}$, —OS(O)$_2$O$^{31}$, —OS(O)$_2$R$^{54}$, —P(O)(O—)$_2$, —P(O)(OR$^{14}$)(O$^{31}$), —OP(O)(OR$^{54}$)(OR$^{55}$), —C(O)R$^{54}$, —C(S)R$^{54}$, —C(O)OR$^{54}$, —C(O)NR$^{54}$R$^{55}$, —C(O)O$^-$, —C(S)OR$^{54}$, —NR$^{56}$C(O)NR$^{54}$R$^{55}$, —NR$^{56}$C(S)NR$^{54}$R$^{55}$, —NR$^{57}$C(NR$^{56}$)NR$^{54}$R$^{55}$, and —C(NR$^{56}$)NR$^{54}$R$^{55}$, where each X is independently a halogen; each R$^{54}$, R$^{55}$, R$^{56}$ and R$^{57}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{58}$R$^{59}$, —C(O)R$^{58}$ or —S(O)$_2$R$^{58}$ or optionally R$^{58}$ and R$^{59}$ together with the atom to which they are both attached form a cycloheteroalkyl or substituted cycloheteroalkyl ring; and R$^{58}$ and R$^{59}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl.

"Sulfate" refers to a radical —OS(O)(O)OR, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Sulfonamide" refers to a radical —S(O)(O)NR'R", where R' and R" are independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein or optionally R' and R" together with the atom to which they are both attached form a cycloheteroalkyl or substituted cycloheteroalkyl ring. Representative examples include but not limited to azetidinyl, pyrrolidinyl, piperidinyl, morpholinyl, 4-(NR''')-piperazinyl or imidazolyl group wherein said group may be optionally substituted by one or more substituents as defined herein. R''' hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Sulfonate" refers to a radical —S(O)(O)OR, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Thio" means the radical —SH.

"Thioether" refers to a radical —SR, where R is alkyl, cycloalkyl, cycloheteroalkyl, aryl, arylalkyl, heteroalkyl, heteroaryl, heteroarylalkyl, as defined herein that may be optionally substituted by one or more substituents as defined herein.

As used herein, the terms "treat" or "treatment" are used interchangeably and are meant to indicate a postponement of development of arthritis, rheumatoid arthritis, or inflammatory disease and/or a reduction in the severity of such symptoms that will or are expected to develop. The terms further include ameliorating existing symptoms of arthritis or rheumatoid arthritis, preventing additional symptoms, and ameliorating or preventing the underlying metabolic causes of symptoms.

As used herein, the term "subject" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

The term "optional" or "optionally" means that the subsequently described event or circumstance may or may not occur, and that the description includes instances where the event or circumstance occurs and instances where it does not. For example, the phrase "optionally another drug" means that the patient may or may not be given a drug other than the phenazine compounds of the invention. "Another drug" as used herein is meant any chemical material or compound suitable for administration to a mammalian, preferably human, which induces a desired local or systemic effect.

II. Compounds of the Invention

The compounds of the invention include compounds having the structure of Formula I:

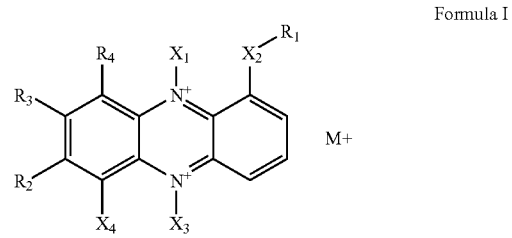

Formula I where X$_1$ and X$_3$ are independently selected to be O$^-$ or S$^-$;
X$_2$ and X$_4$ are independently selected to be O, S, NH, NR$_5$ or CHR$_5$ where R$_5$ can be a lower alkyl;
R$_1$ is selected from the group consisting of lower alkyl containing 1 to 10 carbon atoms, halo-lower alkyl, lower alkenyl, lower alkynyl, lower alkylsulfinyl, lower alkylsulfonyl, lower alkylthio, lower alkylamino, arylalkyl, substituted arylalkyl, cycloalkyl, substituted cycloalkyl, cycloheteroalkyl, substituted cycloheteroalkyl, heteroaryl, or substituted heteroaryl;
R$_2$, R$_3$ and R$_4$ are independently selected to be hydrogen, lower alkyl, substituted lower alkyl, aryl, substituted aryl, arylalkyl, substituted arylalkyl, cycloalkyl, cyano, ether, halo, hydroxy, phosphate, phosphonate, sulfate, sulfonate, or sulfonamide; and M+ is alkali metal ion such as sodium, lithium, and potassium, alkaline earth metal ion such as calcium and magnesium, or any other positively charged species that forms a pharmaceutically acceptable salt.

In another aspect, the compounds of the invention include compounds having the structure of Formula II:

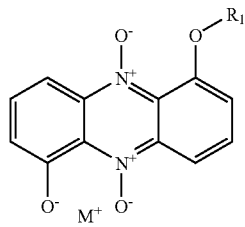

Formula II where $R_1$ is lower alkyl containing 1 to 10 carbon atoms, halo-lower alkyl, lower alkenyl, lower alkynyl, lower alkylamino, cycloalkyl, or heteroaryl; and $M^+$ is $Na^+$, $K^+$, or any other positively charged species that forms a pharmaceutically acceptable salt. Preferably $R_1$ is methyl, ethyl, $^n$propyl, or $^n$butyl, more preferably methyl. Thus, the phenazine compounds are preferably of the structure of Formulae III or IV:

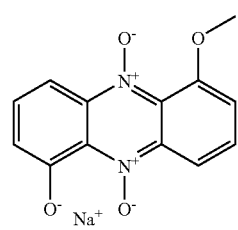

Formula III

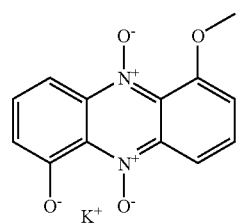

Formula IV

The phenazine compounds of the invention do not include the compounds illustrated by the following structures:

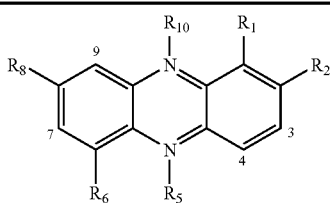

| Name | $R_1$ | $R_2$ | $R_5$ | $R_6$ | $R_8$ | $R_{10}$ |
|---|---|---|---|---|---|---|
| Myxin | H | H | O | $OCH_3$ | H | O |
| Iodinin | OH | H | O | OH | H | O |
| Pyocyanate | OH | H | $CH_3$ | H | H | — |
| HemiPyocyanate | OH | H | — | H | H | — |

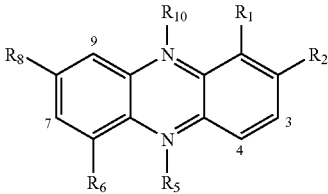

| Name | $R_1$ | $R_2$ | $R_5$ | $R_6$ | $R_8$ | $R_{10}$ |
|---|---|---|---|---|---|---|
| Tubermycin B | COOH | H | — | H | H | H |
| Choraphin | $CONH_2$ | H | H | H | H | H |
| Oxychloraphin | $CONH_2$ | H | — | H | H | — |
| Aeruginosin A | H | $NH_2$ | — | COOH | H | $CH_3$ |
| Aeruginosin B | H | $NH_2$ | — | COOH | $SO_3H$ | $CH_3$ |

In another aspect of the invention, rational drug design, based upon structural studies of the molecular shapes of the compounds of Formulae II, III and IV identified above, and known ligands or analogs can be used to identify compounds whose three-dimensional structure is complementary to that of compounds of Formulae II, III and IV and could thus have the same activity. These additional compounds can be determined by a variety of techniques, including molecular mechanics calculations, molecular dynamics calculations, constrained molecular dynamics calculations in which the constraints are determined by NMR spectroscopy, distance geometry in which the distance matrix is partially determined by NMR spectroscopy, x-ray diffraction, or neutron diffraction techniques.

Computer programs for use in rational drug design include but are not limited to AMBER (available from University of California, San Francisco), CHARMM (Chemistry at HARvard Molecular Mechanics, available from Harvard University), MM2, SYBYL (Trypos Inc.), CHEMX (Chemical Design), MACROMODEL, GRID (Molecular Discovery Ltd), and Insight II (Accelry). Such programs are contemplated as being useful for the determination of the chemical interaction between two molecules, either isolated, or surrounded by solvent molecules, such as water molecules, or using calculations that approximate the effect of solvating the interacting molecules. The relative orientation of the two can be determined manually, by visual inspection, or by using other computer programs which generate a large number of possible orientations. Examples of computer programs include but are not limited to DOCK and AutoDOCK. Each orientation can be tested for its degree of complementarity using the computer programs. Thus, novel compounds can be designed that can be represented by Formulae I-IV.

Other methods for identifying compounds of Formulae I-IV involve the use of techniques such as UV/VIS spectroscopy, polarimetry, CD or ORD spectroscopy, IR or Raman spectroscopy, NMR spectroscopy, fluorescence spectroscopy, HPLC, gel electrophoresis, capillary gel electrophoresis, dialysis, refractometry, conductometry, atomic force microscopy, polarography, dielectometry, calorimetry, solubility, EPR, surface plasmon resonance, or mass spectroscopy.

The compounds of Formulae I-IV thus identified or designed can be subsequently tested for their ability to treat and/or prevent autoimmune diseases or inflammatory diseases. In one aspect, the computer based methods discussed above are used. In another method, the compounds are tested for their ability to treat and/or prevent autoimmune diseases or inflammatory diseases. Lead compounds identified during these screens can serve as the basis for the synthesis of more active analogs. Lead compounds and/or active analogs generated therefrom can be formulated into pharmaceutical compositions effective in treating and/or preventing autoimmune diseases or inflammatory diseases.

III. Synthesis of the Phenazine Compounds

In general, the phenazine compounds can be biosynthesized using a variety of organisms, such as mold, algae, and bacteria. In organisms, the biosynthesis of the phenazine compounds branches off the shikimic acid pathway subsequent to chorismic acid. Two molecules of the chorismate-derived intermediate are brought together in a diagonally-symmetrical fashion to form the basic phenazine scaffold. Sequential modifications then lead to a variety of phenazines with differing biological activities. Thus, in one aspect of the invention, an organism is either selected or created using known biotechnology methods and protocols such that the organism can modify the basic phenazine scaffold to the particular compounds of interest.

Thus, an organism or a subisolate once identified can be grown under fermentation conditions to synthesize the desired compounds. The fermentation medium consists of sources of carbon, nitrogen, minerals, and growth factors. Examples of suitable carbon sources include glycerol and various simple sugars such as glucose, mannose, fructose, xylose, ribose, and other carbohydrate-containing materials such as dextrin, starch, cornmeal, and whey, and cellulose containing medium including papers and newspaper. Normally, the quantity of carbon source materials in the fermentation medium varies from about 0.1 to about 10 percent by weight. Suitable nitrogen sources in the fermentation medium include organic, inorganic, and mixed inorganic-organic nitrogen-containing materials. Examples of such materials are cottonseed meal, soybean meal, corn germ flour, corn steep liquor, distillers dry solubles, peanut meal, peptonized milk, caseins and various ammonium salts. The addition of minerals and growth factors can also be helpful in the production of the bioactive compounds of the invention. Examples of suitable minerals and growth factors include potassium chloride, calcium chloride, sodium chloride, ferrous sulfate, calcium carbonate, cobaltous chloride, zinc sulfate, and various yeast and milk products. The product can be isolated from the aqueous layer using an organic solvent, where the organic solvents can be benzene, hexane, ethyl acetate, acetone, acetonitrile, chloroform, dichloromethane, other organic solvents and extraction buffers.

In another aspect of the invention, the bioactive compounds of the invention can be produced by solid-state fermentation of the microorganism. In another aspect of the invention, the phenazine compounds of the present invention, and other related compounds having different substituents identified by any of the methods described above can be chemically synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTRY 3$^{rd}$ Ed., Vols. A and B (Plenum 1992), and Green and Wuts, PROTECTIVE GROUPS IN ORGANIC SYNTHESIS 2$^{nd}$ Ed. (Wiley 1991). Starting materials for the compounds of the invention may be obtained using standard techniques and commercially available precursor materials, such as those available from Aldrich Chemical Co. (Milwaukee, Wis.), Sigma Chemical Co. (St. Louis, Mo.), Lancaster Synthesis (Windham, N.H.), Apin Chemicals, Ltd. (New Brunswick, N.J.), Ryan Scientific (Columbia, S.C.), Maybridge (Cornwall, England) and Trans World Chemicals (Rockville, Md.).

The procedures described herein for synthesizing the compounds of the invention may include one or more steps of protection and deprotection (e.g., the formation and removal of acetal groups). In addition, the synthetic procedures disclosed below can include various purifications, such as column chromatography, flash chromatography, thin-layer chromatography (TLC), recrystallization, distillation, high-pressure liquid chromatography (HPLC) and the like. Also, various techniques well known in the chemical arts for the identification and quantification of chemical reaction products, such as proton and carbon-13 nuclear magnetic resonance ($^1$H and $^{13}$C NMR), infrared and ultraviolet spectroscopy (IR and UV), X-ray crystallography, elemental analysis (EA), HPLC and mass spectroscopy (MS) can be used as well. Methods of protection and deprotection, purification and identification and quantification are well known in the chemical arts.

Prodrugs and solvates of the compounds of the invention are also contemplated herein. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The transformation a compound (e.g, a drug precursor) in vivo to yield a compound of Formulae I-IV can occur by various mechanisms (e.g., by metabolic or chemical processes), such as, for example, through hydrolysis in blood. For example, if a compound of Formula I-IV or a pharmaceutically acceptable salt, hydrate or solvate of the compound contains a carboxylic acid functional group, a prodrug can comprise an ester formed by the replacement of the hydrogen atom of the acid group with a group such as, for example, $(C_1$-$C_{10})$alkyl, lower alkanoyloxymethyl, $(C_4$-$C_{10})$1-(alkanoyloxy)ethyl, $(C_5$-$C_{10})$1-methyl-1-(alkanoyloxy)-ethyl, $(C_3$-$C_{10})$alkoxycarbonyloxymethyl, $(C_4$-$C_8)$1-(alkoxycarbonyloxy)ethyl, $(C_5$-$C_{10})$1-methyl-1-(alkoxycarbonyloxy) ethyl, and the like.

In another aspect, the present invention is directed to a pharmaceutical composition comprising a therapeutically effective amount of at least one compound of Formula I-IV, or a pharmaceutically acceptable salt, solvate, ester, or tautomer thereof, and at least one pharmaceutically acceptable carrier.

In yet another aspect, the present invention is directed to a method of treating a disease or disorder in a patient, such as metabolic syndrome, dyslipidemia, cardiovascular diseases, disorders of the peripheral and central nervous system, hematological diseases, cancer, inflammation, respiratory diseases, gastroenterological diseases, diabetes, and non-alcoholic fatty liver disease. The method comprises administering to the patient an effective amount of at least one compound of Formula I-IV, or a pharmaceutically acceptable salt, solvate, ester, or tautomer thereof. Preferred diseases that may be treated by the methods include inflammatory or immunological disease, for example, rheumatoid arthritis, osteoarthritis, ankylosing spondylitis, psoriasis, psoriatic arthritis, asthma, acute respiratory distress syndrome, chronic obstructive pulmonary disease, or multiple sclerosis. Additional preferred diseases that may be treated by the methods include diabetes, hyperlipidemia, including coronary heart disease, cancer or proliferative disease.

IV. Pharmaceutical Formulations and Modes of Administration

The methods described herein use pharmaceutical compositions comprising the molecules described above, where the molecule is preferably Formula I, II, II, or IV described in detail above, together with one or more pharmaceutically acceptable excipients or vehicles, and optionally other therapeutic and/or prophylactic ingredients. Such excipients include liquids such as water, saline, glycerol, polyethyleneglycol, hyaluronic acid, ethanol, etc. Suitable excipients for non-liquid formulations are also known to those of skill in the art. Pharmaceutically acceptable salts can be used in the compositions of the present invention and include, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients and salts is available in *Remington's Pharmaceutical Sciences*, 18th Edition (Easton, Pa.: Mack Publishing Company, 1990).

Additionally, auxiliary substances, such as wetting or emulsifying agents, biological buffering substances, surfactants, and the like, can be present in such vehicles. A biological buffer can be any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, the pharmaceutical compositions can be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, may include other pharmaceutical agents, adjuvants, diluents, buffers, etc.

The invention includes a pharmaceutical composition comprising a compound of the present invention including isomers, racemic or non-racemic mixtures of isomers, or pharmaceutically acceptable salts or solvates thereof together with one or more pharmaceutically acceptable carriers, and optionally other therapeutic and/or prophylactic ingredients.

In general, the compounds of this invention will be administered in a therapeutically effective amount by any of the accepted modes of administration. Suitable dosage ranges depend upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compounds of this invention for a given disease.

Thus, the compounds of this invention can be administered as pharmaceutical formulations including those suitable for oral (including buccal and sub-lingual), rectal, nasal, topical, pulmonary, vaginal or parenteral (including intramuscular, intraarterial, intrathecal, subcutaneous and intravenous) administration or in a form suitable for administration by inhalation or insufflation. The preferred manner of administration is intravenous or oral using a convenient daily dosage regimen which can be adjusted according to the degree of affliction.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, referenced above.

For oral administration, the composition will generally take the form of a tablet, capsule, a softgel capsule or can be an aqueous or nonaqueous solution, suspension or syrup. Tablets and capsules are preferred oral administration forms. Tablets and capsules for oral use can include one or more commonly used carriers such as lactose and corn starch. Lubricating agents, such as magnesium stearate, are also typically added. Typically, the compounds of the invention can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Thus, for example, capsules can be prepared by conventional procedures so that the dosage unit is 100 mg of the compounds of the invention, 100 mg of cellulose and 10 mg of magnesium stearate. A large number of unit capsules may also prepared by filling standard two-piece hard gelatin capsules each with 100 mg of powdered active ingredient, 150 mg of lactose, 50 mg of cellulose, and 10 mg magnesium stearate. Or, tablets may be prepared by conventional procedures so that the dosage unit is 100 mg of the compounds of the invention, 150 mg of lactose, 50 mg of cellulose and 10 mg of magnesium stearate. A large number of tablets may also be prepared by conventional procedures such that the dosage unit was 100 mg of the compounds of the invention, and other ingredients can be 0.2 mg of colloidal silicon dioxide, 5 mg of magnesium stearate, 250 mg of microcrystalline cellulose, 10 mg of starch and 100 mg of lactose. Appropriate coatings may be applied to increase palatability or delay absorption.

When liquid suspensions are used, the active agent can be combined with any oral, non-toxic, pharmaceutically acceptable inert carrier such as ethanol, glycerol, water, and the like and with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils, fatty esters or polyols are conventionally employed as solvents or suspending media. In addition, parenteral administration may involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the present invention into the body of a patient through a needle or a catheter, propelled by a sterile syringe or some other mechanical device such as an continuous infusion system. A formulation provided by the present invention can be administered using a syringe, injector, pump, or any other device recognized in the art for parenteral administration.

Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They can be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

The formulations can optionally contain an isotonicity agent. The formulations preferably contain an isotonicity agent, and glycerin is the most preferred isotonicity agent. The concentration of glycerin, when it is used, is in the range known in the art, such as, for example, about 1 mg/mL to about 20 mg/mL.

The pH of the parenteral formulations can be controlled by a buffering agent, such as phosphate, acetate, TRIS or L-arginine. The concentration of the buffering agent is preferably adequate to provide buffering of the pH during storage to maintain the pH at a target pH±0.2 pH unit. The preferred pH is between about 7 and about 8 when measured at room temperature.

Other additives, such as a pharmaceutically acceptable solubilizers like Tween 20® (polyoxyethylene (20) sorbitan monolaurate), Tween 40® (polyoxyethylene (20) sorbitan monopalmitate), Tween 80® (polyoxyethylene (20) sorbitan monooleate), Pluronic F68® (polyoxyethylene polyoxypropylene block copolymers), and PEG (polyethylene glycol) can optionally be added to the formulation, and may be useful if the formulations will contact plastic materials. In addition, the parenteral formulations can contain various antibacterial and antifungal agents, for example, parabens, chlorobutanol, phenol, sorbic acid, thimerosal, and the like.

Sterile injectable solutions are prepared by incorporating one or more of the compounds of the invention in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Thus, for example, a parenteral composition suitable for administration by injection is prepared by stirring 1.5% by weight of active ingredient in 10% by volume propylene glycol and water. The solution is made isotonic with sodium chloride and sterilized.

Alternatively, the pharmaceutical compositions of the invention can be administered in the form of suppositories for rectal administration. These can be prepared by mixing the agent with a suitable nonirritating excipient which is solid at room temperature but liquid at the rectal temperature and therefore will melt in the rectum to release the drug. Such materials include cocoa butter, beeswax and polyethylene glycols.

The pharmaceutical compositions of the invention can also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, propellants such as fluorocarbons or nitrogen, and/or other conventional solubilizing or dispersing agents.

Preferred formulations for topical drug delivery are ointments and creams. Ointments are semisolid preparations which are typically based on petrolatum or other petroleum derivatives. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Formulations for buccal administration include tablets, lozenges, gels and the like. Alternatively, buccal administration can be effected using a transmucosal delivery system as known to those skilled in the art. The compounds of the invention may also be delivered through the skin or muscosal tissue using conventional transdermal drug delivery systems, i.e., transdermal "patches" wherein the agent is typically contained within a laminated structure that serves as a drug delivery device to be affixed to the body surface. In such a structure, the drug composition is typically contained in a layer, or "reservoir," underlying an upper backing layer. The laminated device may contain a single reservoir, or it may contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or gel reservoir, or may take some other form. The backing layer in these laminates, which serves as the upper surface of the device, functions as the primary structural element of the laminated structure and provides the device with much of its flexibility. The material selected for the backing layer should be substantially impermeable to the active agent and any other materials that are present.

The compounds of the present invention can be formulated for aerosol administration, particularly to the respiratory tract and including intranasal administration. The compound will generally have a small particle size for example of the order of 5 microns or less. Such a particle size may be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

A pharmaceutically or therapeutically effective amount of the composition will be delivered to the subject. The precise effective amount will vary from subject to subject and will depend upon the species, age, the subject's size and health, the nature and extent of the condition being treated, recommendations of the treating physician, and the therapeutics or combination of therapeutics selected for administration. Thus, the effective amount for a given situation can be determined by routine experimentation. For purposes of the present invention, generally a therapeutic amount will be in the range of about 0.01 mg/kg to about 40 mg/kg body weight, more preferably about 0.1 mg/kg to about 10 mg/kg, in at least one dose. In larger mammals the indicated daily dosage can be from about 1 mg to 300 mg, one or more times per day, more preferably in the range of about 10 mg to 200 mg. The subject may be administered as many doses as is required to reduce and/or alleviate the signs, symptoms, or causes of the disorder in question, or bring about any other desired alteration of a biological system.

When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

V. Other Agents

The compounds of Formula I-IV, or pharmaceutically acceptable salts, solvates, or esters thereof, can also be administered in combination with other therapeutic agents. For example one or more compounds of Formula I-IV or pharmaceutically acceptable salts, solvates, or esters thereof, can be administered with one or more additional active ingredients selected from the group consisting of HMG CoA reductase inhibitor compounds, HMG CoA synthetase inhibitors, squalene synthesis inhibitors, squalene epoxidase inhibitors, sterol biosynthesis inhibitors, nicotinic acid derivatives, bile acid sequestrants, AcylCoA:Cholesterol O-acyltransferase inhibitors, cholesteryl ester transfer protein inhibitors, fish oils containing Omega 3 fatty acids, plant stanols and/or fatty acid esters of plant stanols, anti-oxidants, PPAR agonists, FXR receptor modulators, LXR receptor agonists, lipoprotein synthesis inhibitors, renin angiotensin inhibitors, microsomal triglyceride transport protein inhibitors, bile acid reabsorption inhibitors, triglyceride synthesis inhibitors, squalene epoxidase inhibitors, low density lipoprotein receptor inducers or activators, platelet aggregation inhibitors, 5-LO or FLAP inhibitors, niacin or niacin receptor agonists, 5HT transporter inhibitors, NE transporter inhibitors, NPY1 antagonists, NPY5 antagonists, NPY2 agonists, NPY4 agonists, leptins, leptin agonists/modulators, leptin derivatives, opioid antagonists, CNTF, CNTF derivatives, CNTF agonists/modulators, serotonin reuptake inhibitors, GLP-1 agonists, PDE inhibitors, UCP activators, lipase inhibitors, fatty acid transporter inhibitors, dicarboxylate transporter inhibitors, glucose transporter inhibitors, phosphate transporter inhibitors, anti-diabetic agents, anti-hypertensive agents, anti-dyslipidemic agents, apolipoprotein-B secretion/microsomal triglyceride transfer protein (apo-B/MTP) inhibitors, dopamine agonists, apo A1 milano reverse cholesterol transport inhibitors, fatty acid binding protein inhibitors (FABP), and fatty acid transporter protein inhibitors (FATP), and the like. In another aspect, the additional active agent can be, but is not limited to, an estrogen, an IGF, osteoprotegrin (OPG), a calcitonin, a bisphosphonate, vitamin $D_3$ or an analogue thereof, a statin, an adrogen, a fluoride salt, a vitamin, a mineral supplement, a nutritional supplement, and combinations thereof. The additional agent also may be an antibiotic such as gentamycin, ciprofloxacin, vancomycin, and/or others. This additional active agent can be administered to the subject prior to, concurrently with or subsequently to administration of the compounds of Formula I-IV of this invention. Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention.

In the case of autoimmune disease, inflammation, inflammatory diseases, and other such cytokine mediated disorders, the additional agent(s) can be selected from the group consisting of a nonsteroidal anti-inflammatory drug (NSAID) (such as diclofenac, diflunisal, ibuprofen, naproxen and the like), a cyclooxygenase-2 inhibitor (such as celecoxib, rofecoxib and the like), a corticosteroid (such as prednisone, methylprednisone and the like) or other immunosuppressive agent (such as methotrexate, leflunomide, cyclophosphamide, azathioprine and the like), a disease-modifying anti-rheumatic drug (DMARD) (such as injectable gold, penicilliamine, hydroxychloroquine, sulfasalazine and the like), a TNF-alpha inhibitor (such as etanercept, infliximab and the like), other cytokine inhibitor (such as soluble cytokine receptor, anti-cytokine antibody and the like), other immune modulating agent (such as cyclosporin, tacrolimus, rapamycin and the like) and a narcotic agent (such as hydrocodone, morphine, codeine, tramadol and the like).

In the case of hyperlipidemia, diabetes, insulin resistance and associated conditions or complications, including obesity, such additional agent(s) can be selected from the group consisting of insulin or an insulin mimetic, a sulfonylurea (such as acetohexamide, chlorpropamide, glimepiride, glipizide, glyburide, tolbutamide and the like) or other insulin secretagogue (such as nateglinide, repaglinide and the like), a thiazolidinedione (such as pioglitazone, rosiglitazone and the like) or other peroxisome proliferator-activated receptor (PPAR) agonist, a fibrate (such as bezafibrate, clofibrate, fenofibrate, gemfibrozol and the like), a biguanide (such as metformin), a statin (such as fluvastatin, lovastatin, pravastatin, simvastatin and the like) or other hydroxymethylglutaryl (HMG) CoA reductase inhibitor, an alpha-glucosidase inhibitor (such as acarbose, miglitol, voglibose and the like), a bile acid-binding resin (such as cholestyramine, celestipol and the like), a high density lipoprotein (HDL)-lowering agent such as apolipoprotein A-I (apoA1), niacin and the like, probucol and nicotinic acid. Preferred additional agents include, for example, sulfonylurea, thiazolidinedione, fibrate or statin.

Non-limiting examples of HMG CoA reductase inhibitor compounds useful in combination with the compounds of Formula I-IV of the present invention are lovastatin (for example MEVACOR® which is available from Merck & Co.), simvastatin (for example ZOCOR® which is available from Merck & Co.), pravastatin (for example PRAVACHOL® which is available from Bristol Meyers Squibb), atorvastatin, fluvastatin, cerivastatin, CI-981, rivastatin (sodium 7-(4-fluorophenyl)-2,6-diisopropyl-5-methoxymethylpyridin-3-yl)-3,5-dihydroxy-6-heptanoate), rosuvastatin calcium (CRESTOR® from AstraZeneca Pharmaceuticals), pitavastatin (such as NK-104 of Negma Kowa of Japan), and the like.

A non-limiting example of a HMG CoA synthetase inhibitor useful in combination with the compounds of Formula I-IV of the present invention is, for example, L-659,699 ((E, E)-11-[3'R-(hydroxy-methyl)-4'-oxo-2'R-oxetanyl]-3,5,7R-trimethyl-2,4-undecadienoic acid), and the like.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1

Microorganisms for Synthesizing Phenazine Derivatives

The compounds of the invention were synthesized using microorganisms, particularly a subisolate from *Lysobacter antibioticus* ATCC(r) 9311 (29479), and designated MC-4. MC-4 was isolated by growing *Lysobacter antibioticus* ATCC(r) 9311 (29479) in an SD-38 an agar plate (Table 1) (0.3% casein; 0.25% brewers yeast; 0.13% $CaCl_2$) fermentation medium, shaken for 24 hrs.

TABLE 1

| Formulation of agar culture medium (ACM) | |
|---|---|
| casein | 0.30% |
| brewers yeast | 0.25% |
| calcium chloride | 0.13% |
| Agar | 1.50% |
| Distilled Water | |

MC-4 was transferred to an agar slant of the same medium composition and incubated at 28° C. After 24 hrs of cultivation, 10 ml of the fermentation broth was mixed with 5 ml of methylene chloride and allowed to settle into phases. The mixture was allowed to incubate for 3 days at room temperature (lab bench). The upper aqueous phase showed noticeable growth, and was subsequently spread plated on to SD-38 agar plate, and allowed to incubate for 7 days at 28 C. Several colonies were isolated including MC-4 (brown colony with black dot in center; colony produces dark heavy pigment).

The compound of Formula III or IV was produced using aerobic fermentation of MC-4 subisolate under controlled conditions.

The Fermentative Production of the Bioactive Compound

The compound of Formula III or IV was produced using aerobic fermentation of MC-4 subisolate under controlled conditions.

One method for the aerobic fermentation of MC-4 subisolate utilized the submerged culture fermentation method. The fermentation medium was prepared by dissolving or suspending the ingredients in water and subsequently sterilizing the resulting medium by autoclaving or by steam heating. The sterilized medium was cooled to a temperature of between 16° C. and 45° C., inoculated with the microorganism, and thereafter fermentation was carried out with aeration and agitation using either shake-flasks or stationary tank fermentors. In shake-flasks, aeration is achieved by agitating the flasks to bring about intimate mixing of the inoculated medium with air. In stationary tank fermentors, agitation is provided by impellers, which may take the form of disc turbines, vaned discs, or open turbine or marine propellers. Aeration is accomplished by sparging air or oxygen into the agitated mixture. The fermentation was allowed to proceed for a period of from 10-48 hrs.

Shake-Flask Fermentation

A portion of the microbial growth from the agar slant (above) was used to inoculate an 18-mm.×150-mm seed tube containing 5 ml of seed medium SCM (Table 2).

TABLE 2

| Formulation of seed culture medium (SCM) | |
|---|---|
| casein | 0.30% |
| brewers yeast | 0.25% |
| calcium chloride | 0.13% |
| Distilled Water | |

The inoculated seed was shaken at 28° C. for 16-24 hrs. A 1-ml portion of the microbial growth from the seed tube was transferred to a 300-ml Tunair Ful-Baf flask containing 100 ml of production culture medium (PCM, Table 3):

TABLE 3

| Formulation of production culture medium (CPM) | |
|---|---|
| casein | 0.30% |
| brewers yeast | 0.25% |
| calcium chloride | 0.13% |
| Tap Water | |

The inoculated flask was incubated at 28° C. for 16-24 hrs shaking (180 rpm gyratory shaker, 5-cm throw). Production of the precursor to the compound of Formula III or IV was observed for the first time in this broth.

The biological activity of the fermentation broths was assayed by the agar diffusion assay involving *Saccharomyces cerevisiae* (RSY) and *Aspergillus terreus* (MEVS).

25-Gal Stirred-Jar Fermentation

A cryogenic vial containing approximately 1 ml of a suspension of the culture was used to inoculate 100 ml of seed culture medium (SCM) in a 300-ml Tunair Ful-Baf shake flask. The inoculated flask was incubated for about 16-24 hours at 28° C. for 16-24 hrs shaking (180 rpm gyratory shaker, 5-cm throw).

After sufficient growth is obtained, 10-ml aliquots of the microbial growth were transferred aseptically to four 2-L Erlenmeyer seed flasks containing a 500-ml of SCM. The inoculated medium was incubated at 28° C. for 16-24 hrs shaking (180 rpm gyratory shaker, 5-cm throw).

The microbial growth from these four flasks were pooled and used to inoculate a 25-gal Airmentor. The production fermentor contained 20 gallons (80 liters) of production culture medium (CPM), which was 'steam sterilized' for 40 minutes at 121.degree. C. The medium was cooled to 28° C. before inoculation. Fermentation was carried out for about 20 hrs., stirred at 155 rpm, and sparged with air at 1 CFM air. A silicone-based antifoam was used to control foaming as needed.

Chemical Isolation of the Compound.

The fermentation broth (80 liters) prepared as described above was transferred to a holding tank containing 30 L of methylene chloride and stirred intermittently. Extraction of the compound was allowed overnight. After allowing the mixture to separate, the lower organic layer was removed. The methylene chloride extract was concentrated to slurry, and then filter aid was added.

The air dried crude sample was allowed to air dry, then charged to a silica gel column: 1 part sample and 10 parts silica gel (200-300 mesh, Natland, N.C.). After packing the silica gel column with the sample, the column was eluted with methylene chloride. The column resolved different bands including cherry pink, orange, tan, pink, yellow, and brown bands. The rich cut eluate containing the pink band was recovered and dried in vacuo to provide 1.5 g of a compound.

1 gram of the compound thus obtained was dissolved in 50 ml acetone and 1 gram of NaOH (slurried in minimal water) was added to the solution. The mixture was stirred for about 1 hour, the precipitate recovered by centrifugation; and the precipitate washed 3× with acetone or until the acetone wash was clear. The dark green precipitate thus obtained was air dried to yield about 1.5 gram of compound of Formula III. Compound of Formula IV can be prepared by using KOH.

Example 2

Anti-Arthritic Activity

Collagen-Induced Arthritis Mouse Model

Type II collagen-induced arthritis (CIA) in mice is an accepted experimental model of arthritis with a number of pathological, immunological and genetic features in common with rheumatoid arthritis. This disease is induced by immunization of susceptible strains of mice with type II collagen, the major component of joint cartilage. A progressive, inflammatory arthritis develops in the majority of immunized animals, which is characterized clinically by erythema and edema, with affected paw width increases of typically 100%. A clinical scoring index has been developed to assess disease progression to joint distortion and spondylitis. Histopathology of affected joints reveals synovitis, pannus formation, and cartilage and bone erosion, which may also be represented by an index. Immunological laboratory findings include high antibody levels to type II collagen and hypergammaglobulinemia.

This study was designed to evaluate the anti-inflammatory and anti-arthritic activity of compound of Formula III using the CIA model by observing changes in immune parameters due to treatment. The animals were administered oral corticosteroid, Enbrel, an injectable TNF inhibitor, and compound of Formula III using both oral and parenteral delivery. Seventy-five DBA/1 LacJ mice 8-10 weeks of age were obtained from Jackson Labs and quarantined in our facility for 10 days prior to experimentation. All mice weighed >16 grams at the start of the experiment. Mice were pre-bled by retro-orbital puncture, and injected with 100 µg Bovine type II collagen in Freund's complete adjuvant (FCA) intradermally at the base of the tail. Mice were monitored by daily examination for the onset of disease. Mice that developed CIA between 20 days post immunization and 42 days post immunization were assigned to one of five treatment groups on a rotational basis (to normalize onset date), and ten mice were assigned to each group. For administration, compound of Formula III was solubilized in sterile saline. To facilitate drugs delivered by oral administration, carboxymethylcellulose was added to a final concentration of 4% in all gavage solutions. Compounds were administered according to the following schedule:

Group 1. 100 µl sterile saline vehicle injected intraperitoneally (i.p.)×3/week.

Group 2. 100 µl sterile saline containing compound of Formula III at 40 mg/kg injected i.p.×3/week.

Group 3. 100 µl sterile saline containing 100 µg Enbrel injected i.p.×3/week.

Group 4. 100 µl sterile saline containing compound of Formula III at 40 mg/kg gavaged×5/week.

Group 5. 100 µl sterile saline containing prednisolone 10 mg/kg gavaged×5/week.

Mice were weighed weekly, and overall health status noted. Arthritiic animals were clinically assessed by visual inspection five times per week, and paw swelling quantified by caliper measurements made three times per week, until seven weeks after the initial onset of arthritis. All animals were assessed individually from the time of disease onset, and the appropriate findings were entered into clinical report forms.

Immunological Assessment:

All mice were pre-bled prior to the start of the trial, subsequently at onset of arthritis and at the completion of the trial. Sera were separated and stored at −80° C. ELISA assays were performed to determine anti-type II collagen antibody levels and total immunoglobulin levels.

Anti-Collagen Antibody Levels.

ELISA plates (Nunc-Immuno plates, Denmark) were coated with 100 µl of coating buffer (0.4M phosphate buffer ph7.6) containing 5 µg of type II collagen, at 4° C. overnight. Plates were washed 3 times with PBS containing 0.05% Tween 20 (Sigma, St. Louis, Mo.) and non specific binding was blocked by PBS containing 5% non fat milk overnight at 4° C. Mouse sera diluted to 1/100 in 5% milk/PBS was added to each well and incubated overnight at 4° C. Subsequently, the plates were washed six times in PBS containing 0.05% Tween-20 and incubated with alkaline phosphatase conjugated goat anti-mouse Ig (Southern Biotechnology Associates, Birmingham, Ala.) at 37° C. for 1 hour. Plates were washed 6 times again and developed for 40 minutes in the dark, using p-nitrophenyl phosphate (Sigma, St. Louis, Mo.) as a chromatogen substrate. The resulting optical density was measured at 405 nm by using a UV max spectrophotometer (Molecular Devices, CA). Negative pre-bleed control sera and a standard mouse anti-CII antiserum were titered on each plate to ensure uniformity of the assay. Antibody binding was expressed as OD405 units-blank.

Immunoglobulin Levels.

Serum Ig levels was assessed using an ELISA assay. Dynatech Immulon I 96 well ELISA plates were coated with a 1/250 dilution of rabbit anti-mouse IgG (Axell) in PBS overnight at 4° C. Plates were washed ×3 with PBS containing 0.05% Tween, and blocked by the addition of 5% BSA in PBS. Serum samples diluted 1/400 in PBS/BSA was dispensed in triplicate, and a reference curve constructed by a doubling dilution titer of mouse Ig reference serum (Miles) from 1/500 to 1/256,000. The plate was incubated overnight at room temperature, and washed ×3 with PBS/Tween. One hundred µl of goat anti-IgG conjugated with alkaline phosphatase (Fisher-Biotek) (1:500 dilution in Milk/PBS/Tween) was added, and the incubation continued for 1 hour at 37° C. After washing×3 with PBS/Tween, 100 µl of paranitrophenyl phosphate solution (PNPP tablets, Sigma) in diethylolamine buffer was added to each well, and the reaction allowed to proceed for 20 minutes in the dark. The plate was read at 405 nm using a Photospectrometer (Molecular Devices), and the data analyzed using the SOFTmax analytical software package. The standard curve derived from the reference serum was used to calculate Ig levels in the test samples by regression analysis.

Measurement of Serum Cytokine Levels:

Terminal serum cytokines were assayed using commercial kits (R&D Systems, MN). Briefly, ELISA plates were coated with monclonal anti-IL-1, anti-IL-6, or anti-TNF□. Plates were washed 3 times with PBS containing 0.05% Tween 20 (Sigma, St. Louis, Mo.). 50 µl of serum dilute 1:200 in PBS was then added and incubated overnight at 4° C. Subsequently, the plates were washed six times in PBS containing 0.05% Tween-20 and incubated with biotinylated secondary antibody at 37° C. for 1 hour. Plates were washed 6 times and streptavidin-APK was added and incubated at room temperature for 40 minutes. The plates were then washed 6 times and developed for 40 minutes in the dark, using p-nitrophenyl phosphate (Sigma, St. Louis, Mo.) as a chromatogen substrate. The resulting optical density was measured at 405 nm by using a UV max spectrophotometer (Molecular Devices, CA). Cytokine levels were determined by regression analysis against the standard curve provided by the manufacturer.

Cellular Immune Responses:

Spleen and lymph nodes were removed at sacrifice, and mitogen responses to Con A and LPS, and antigen proliferative responses to type II collagen were determined using standard techniques. Lymph nodes and spleens were harvested and 1 ml of cell suspension ($2.5 \times 10^6$/ml) cultured in 12-well tissue culture plates (Costar, Corning, N.Y.) with various stimuli in complete RPMI-1640 medium. Cells were incubated for 3 days at 37° C. in a 5% $CO_2$ atmosphere in the presence of mitogen or antigen. 20 □l of MTT (a mitochondrial enzyme substrate) solution (5 mg/ml; Sigma, St Louis, Mo.) was added per well. After 6 hours, the culture supernatant was discarded, and 200 □l of 10% SDS solution added to each well. After incubation at 37° C. overnight, the optical density at 590 nm was read using a microplate photospectrometer (Molecular Devices, CA). The mean and OD values, which provide a measure of cell proliferation, were recorded for each cell sample with respect to antigen stimulation. Antigen specific responses were expressed as (OD590 [Stimulated Culture]−OD590 [Spontaneous proliferation culture])/OD590 [Spontaneous proliferation culture].

Clinical Finding of Collagen-Induced Arthritis.

Mice were assessed for the progression of disease based upon the number of involved paws (FIG. 1) and the overall arthritis score (FIG. 2). A significant effect was observed for most compounds in this trial when compared with control (saline-treated) animals.

Significant differences in the number of involved paws were observed between the groups commencing at Day 16 after arthritis onset. Mice receiving prednisolone developed a significantly lower number of arthritic paws ($p<0.002$) than control mice, and this difference was continued throughout the study. Mice receiving Enbrel developed a significantly lower number of arthritic paws ($p<0.05$) from Day 25 through Day 28 of the study. The compound of Formula III did not significantly influence the number of involved paws in this study, irrespective of the route of administration.

In contrast to the influence on paw number, the compound of Formula III was observed to exert a marked effect upon the arthritis score in this study (FIG. 2). As expected, both of the established anti-arthritic compounds prednisolone and Enbrel significantly reduced the arthritis score below the level of disease observed in saline control treated mice.

Treatment with Prednisolone achieved a significant reduction ($p<0.02$) in arthritis score from Day 12 post the start of therapy, and reached a highly significant effect ($p<0.001$) at day 17 that was subsequently sustained throughout the remainder of the trial. Treatment with Enbrel achieved a significant reduction ($p<0.02$) in arthritis score from Day 12 post the start of therapy, but a significant effect was not sustained until 23 days of therapy. Treatment with the compound of Formula III via i.p. administration achieved a significant reduction ($p<0.02$) in arthritis score from Day 23 post the start of therapy, and this effect was highly significant ($p<0.007$) at Day 24. A significant reduction in arthritis score was sustained from Day 23 until the end of the trial. Administration of the compound of Formula III by oral gavage did not exert a statistically significant effect upon the arthritis score in this experiment. These findings suggest that the compounds of the invention have significant anti-arthritic effect, and rather than exerting action by suppressing the migration of disease to uninvolved limbs, acts to reduce disease severity in paws with established arthritis. This mechanism of action appears dissimilar to both of the control compounds, Prednisolone and Enbrel.

Anti-Type II Collagen Antibody Levels.

The levels of anti-CII antibody levels in mice prior to experimentation, at the onset of disease (commencement of dosing), and at the termination of the study are shown in FIG. 3. No mice exhibited any detectable levels of anti-CII antibody prior to injection with type II collagen, and all mice developed a strong antibody response following immunization. At the time of the initiation of drug treatment, there was no significant difference in antibody titers between all five groups, indicating equivalence in anti-CII response.

Consistent with previous findings, mice treated with saline exhibited elevated terminal anti-CII levels when compared with the levels seen at disease onset. After seven weeks of treatment, two compounds exerted a suppressive effect on the increase of anti-CII titers. Prednisolone caused a minor decrease in anti-CII levels compared with the titers assayed at disease onset, and the compound of Formula III administered via i.p. resulted in maintenance of titers equivalent to the levels at onset. These results generated a significant reduction ($p<0.01$) when compared with terminal anti-CII levels in the control mice. These results suggest that the compounds of the invention exert activity via the suppression of the anti-collagen antibody response.

Total Immunoglobulin Levels.

The total serum Ig levels assayed in prebleed, onset and terminal blood samples are shown in FIG. 4. As expected, the induction of collagen arthritis was accompanied by a marked elevation of total serum Ig levels. In saline treated mice, serum Ig continued to rise and was assayed at very high levels at the conclusion of the trial. However, these titers were highly variable among the individual mice in the experiment.

Although both Prednisolone and the compound of Formula III i.p. reduced total serum Ig levels at the terminal bleed, this reduction was not significantly different from the levels observed in control mice at either the time of disease onset or the conclusion of the trial. Similarly, the reduction (or increase) in total Ig levels observed in all groups at the termination of the study was not significantly different from the levels assayed at the onset of disease. Therefore, the data does not support a generalized immunosuppressive effect for the compound of Formula III, but further study will be required to clarify the effect upon immunoglobulin production.

Serum Cytokine Levels.

The levels of IL-1β, IL-6, and TNF☐ in terminal bleed sera produced universally low levels, and revealed no variations attributable to the therapy. The standards for all the cytokines assayed yielded consistent and sensitive curves, suggesting that the assay was accurate. However, previous data has indicated that inflammatory cytokines are typically elevated in collagen arthritis, although these levels can be variable. Further study will be required to establish whether the compound of Formula III exerts an anti-arthritic effect via modulation of specific inflammatory cytokines Cellular Immune Responses:

Lymph node cell responses to the mitogens Concanavalin A and LPS, and the antigen response to type II collagen are shown in FIG. 5.

No significant variations in the response to Con A or type II collagen were observed between the treatment groups. A significant reduction ($p<0.05$) in the response to LPS in lymph nodes cells was observed in lymphocytes harvested from mice treated with compound of Formula III i.p.

Spleen cell responses to the mitogens Concanavalin A and LPS, and the antigen response to type II collagen are shown in FIG. 6. No significant effects of any of the compounds administered were observed on the mitogen or antigen responses in spleen cells.

Example 3

Antilipidemic Activity of Compound of Formula III

Eighty-five male Syrian Golden hamsters ($F_1B$ strain, Bio-Breeders, Fitchburg Mass.) approximately 8-10 weeks of age were acclimated to individual hanging polystyrene cages with bedding for 1 week and then fed a semipurified hypercholesterolemic diet (HCD) containing 25% casein, 20% hydrogenated coconut oil, 2% safflower oil, and 0.15% cholesterol by weight for 2 weeks prior to initiation of the experimental treatments (Table 1). Hamsters were then bled (Week 0) following an overnight fast (16 hr) to determine plasma concentrations of total cholesterol, HDL-C, nonHDL-C, and triglycerides and divided into 17 groups (n=5/group) with similar starting plasma HDL-C levels, and administered either compound of Formula II or vehicle once per day for 14 days.

Plasma total cholesterol, HCL-C, nonHDL-C, and triglycerides were then measured at day 8 (prior to gavage that day) and at day 15 (24 hr after last gavage) following and overnight fast (16 hr). Hamsters were maintained in accordance with the guidelines of the Animal Care Committee at the University of Massachusetts-Lowell Research Foundation and the guidelines prepared by the Committee on the Care and Use of Laboratory Animals of the Institute of Laboratory Animal Resources, National Research Council (DHEW publication no 85-23, revised 1985). Hamsters were housed in an environmentally controlled room with an alternating 12-h light/dark cycle and given ad libitum access to food and water except when food is withheld for the experimental protocols.

TABLE 1

Dietary composition of hamster feed[1]

|  | Gm/100 |
| --- | --- |
| Casein | 25.0 |
| L-Methionine | 0.5 |
| Maltodextrin 10 | 12.5 |
| Corn Starch | 15.6 |
| Sucrose | 9.5 |
| Cellulose | 15.0 |
| Coconut Oil (hydrogenated) | 20.0 |
| Safflower Oil | 2.0 |
| Mineral Mix[2] | 3.5 |
| Vitamin Mix[3] | 1.0 |
| Choline Bitartrate | 0.2 |
| Cholesterol | 0.15 |
| Protein (% Energy) | 22 |
| Carbohydrate (% Energy) | 34 |
| Fat (% Energy) | 44 |

[1]Semi-purified diets were supplied by Research Diets, Inc., New Brunswick, NJ.
[2]S10001 = Mineral mix for AIN-76A rodent diet (32).
[3]V10001 = Vitamin mix for AIN-76A rodent diet (32).

Plasma Lipoprotein Cholesterol and Triglyceride Measurements:

Blood was collected via the retro-orbital sinus into heparinized tubes from hamsters fasted for 16 h at days 0, 8, and 15. Plasma was harvested after centrifugation at 1500-×g at room temperature for 10 min and plasma total cholesterol and triglyceride concentrations were measured enzymatically. Plasma LDL cholesterol (combination of very low-density, intermediate, and low-density lipoprotein-cholesterol) was precipitated with phosphotungstate reagent and HDL cholesterol was measured in the supernatant. The concentration of LDL cholesterol was calculated as the difference between plasma TC and HDL cholesterol. The accuracy and precision of the procedures used for the measurements of plasma TC and HDL cholesterol were maintained by participation in the Lipid Standardization Program of the Centers for Disease Control and the National Heart, Blood and Lung Institute (Atlanta, Ga.). All reagents used were supplied by Sigma-Aldrich (St. Louis, Mo.). All assays were performed using a Cobas Mira Plus® (Cobas Mira Plus® is a registered trademark of Roche Diagnostic Systems, Inc.) clinical chemistry autoanalyzer using 10 µl of plasma for each sample (Roche Pharmaceuticals, Basel, Switzerland).

Antilipidemic Profile of Compound of Formula III:

At day 0, all groups were sorted based on similar plasma nonHDL-cholesterol and total cholesterol concentrations and body weights. At day 8 of treatment, the compound of Formula III administered at a concentration of 0.9, 1.8, and 3.6 mg/kg resulted in plasma total cholesterol changes of −27%, −17%, and −21% respectively compared to vehicle control, plasma nonHDL-C changes of −36%, −24%, and −26% respectively compared to vehicle control, plasma HDL-C changes of −2%, 7%, and −4% respectively compared to vehicle control, and plasma triglycerides changes of −37%, −14%, and −20% respectively compared to vehicle control. Thus, the compounds of the invention are useful for the reduction of lipid profiles of patients.

Example 5

Preparation of Tablets

The compound of Formula III (10.0 g) is mixed with lactose (85.5 g), hydroxypropyl cellulose HPC-SL (2.0 g), hydroxypropyl cellulose L-HPC, LH-22 (2.0 g) and purified water (9.0 g), the resulting mixture is subjected to granulation, drying and grading, and the thus obtained granules are mixed with magnesium stearate (0.5 g) and subjected to tablet making, thereby obtaining tablets containing 10 mg per tablet of the compound of Formula III.

Example 6

Administering to a Subject

The tablet prepared in Example 5 is provided to a subject at time 0. One tablet every 24 h is provided for a period of one week. After administration of the third tablet, the subject is exposed to a neurodegenerative event. The treated subject exhibits symptoms of neurological disorder that are less severe compared to the subject that was not treated.

All printed patents and publications referred to in this application are hereby incorporated herein in their entirety by this reference.

While the preferred embodiment of the invention has been illustrated and described, it will be appreciated that various changes can be made therein without departing from the spirit and scope of the invention.

The invention claimed is:

1. A compound of Formula II:

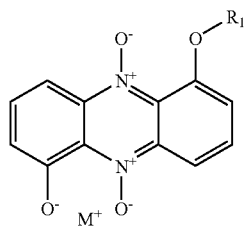

Formula II wherein $R_1$ is lower alkyl consisting of 1 to 10 carbon atoms, halo-lower alkyl, lower alkenyl, lower alkynyl, lower alkylamino, cycloalkyl, or heteroaryl; and $M^+$ is $Na^+$ or $K^+$.

2. The compound of claim 1, wherein $R_1$ is methyl.

3. The compound of claim 1, wherein $M^+$ is $Na^+$.

4. A method of preparing a compound of Formula II:

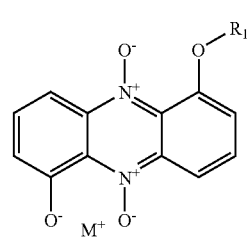

Formula II wherein $R_1$ is lower alkyl consisting of 1 to 10 carbon atoms, halo-lower alkyl, lower alkenyl, lower alkynyl, lower alkylamino, cycloalkyl, or heteroaryl; and $M^+$ is $Na^+$ or $K^+$, the method comprising:
  i) growing *Lysobacter antibioticus* in agar culture medium at a pH range of 4 to 9 and at a temperature range of 15° C. to 37° C.;
  ii) inoculating a production culture medium with *Lysobacter antibioticus*;
  iii) culturing at a pH range of 4 to 9 and at a temperature range of 15° C. to 37° C. with continuous agitation and aeration;
  iv) adding aqueous $M^+OH^-$, wherein $M^+$ is $Na^+$ or $K^+$; and
  v) recovering the compound of Formula II by centrifugation.

5. The method of claim 4, wherein the culturing time is 24 to 200 hours.

6. A method of treating a subject for rheumatoid arthritis or osteoarthritis, the method comprising administering to the subject an effective amount of a compound of Formula II:

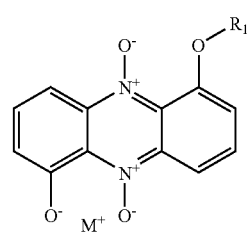

Formula II wherein $R_1$ is lower alkyl consisting of 1 to 10 carbon atoms, halo-lower alkyl, lower alkenyl, lower alkynyl, lower alkylamino, cycloalkyl, or heteroaryl; and $M^+$ is $Na^+$ or $K^+$.

7. The method of claim 6, wherein $R_1$ is methyl.

8. The method of claim 6, wherein $M^+$ is $Na^+$.

9. The method of claim 6, wherein the compound is administered daily.

* * * * *